US00PP32957P2

(12) United States Plant Patent
Van Swieten

(10) Patent No.: US PP32,957 P2
(45) Date of Patent: Apr. 6, 2021

(54) ***PHALAENOPSIS* ORCHID PLANT NAMED 'PHALISYCH'**

(50) Latin Name: ***Phalaenopsis* hybrid**
Varietal Denomination: PHALISYCH

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/910,273

(22) Filed: Jun. 24, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALISYCH', particularly characterized by having yellow flowers with small, dark purplish-pink centers and extra-large, shaded, yellow lips, a flat flower shape in lateral view, petals that are touching to slightly overlapping, and is propagated by meristem tissue culture, is disclosed.

3 Drawing Sheets

Genus and species *Phalaenopsis* hybrid.
Variety denomination: 'PHALISYCH'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALISYCH'.

The new *Phalaenopsis* plant is a product of a planned breeding program conducted by the inventor in Bleiswijk, the Netherlands. The objective of this breeding program was to create a new *Phalaenopsis* plant with numerous attractive and unique yellow flowers with small, dark purplish-pink centers and extra-large, shaded, yellow lips, suitable for potted plant production.

The new *Phalaenopsis* plant 'PHALISYCH' is a result of cross-pollination made by the inventor in July 2014 in Bleiswijk, the Netherlands, of the proprietary female, or seed parent, *Phalaenopsis* hybrid 'E0000298' (unpatented) with the proprietary male, or pollen parent, *Phalaenopsis* hybrid 'E0000299' (unpatented).

The new *Phalaenopsis* was selected by the inventor as a single plant within the progeny of the stated cross-pollination in a controlled greenhouse in Bleiswijk, the Netherlands, in January 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 9, 2020 (Application no. 2020/1006), by Applicant who obtained the subject matter disclosed directly from the inventor. 'PHALISYCH' has not been made publicly available or sold anywhere in the world prior to the effective filing date of this application with the exception of sales or disclosures made one year or less before the effective filing date of this claimed invention by Applicant who obtained 'PHALISYCH' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALISYCH' as a new and distinct variety of *Phalaenopsis* plant:

1) Yellow flowers with small, dark purplish-pink centers;
2) Extra-large, shaded, yellow lips;
3) Flower shape in lateral view is flat; and
4) Arrangement of petals is touching to slightly overlapping.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in April 2020. Colors in the photographs may differ from the color values cited in the detailed botanical description, which accurately describe the actual colors of the new variety.

DESCRIPTION OF THE NEW VARIETY

Figure 1:
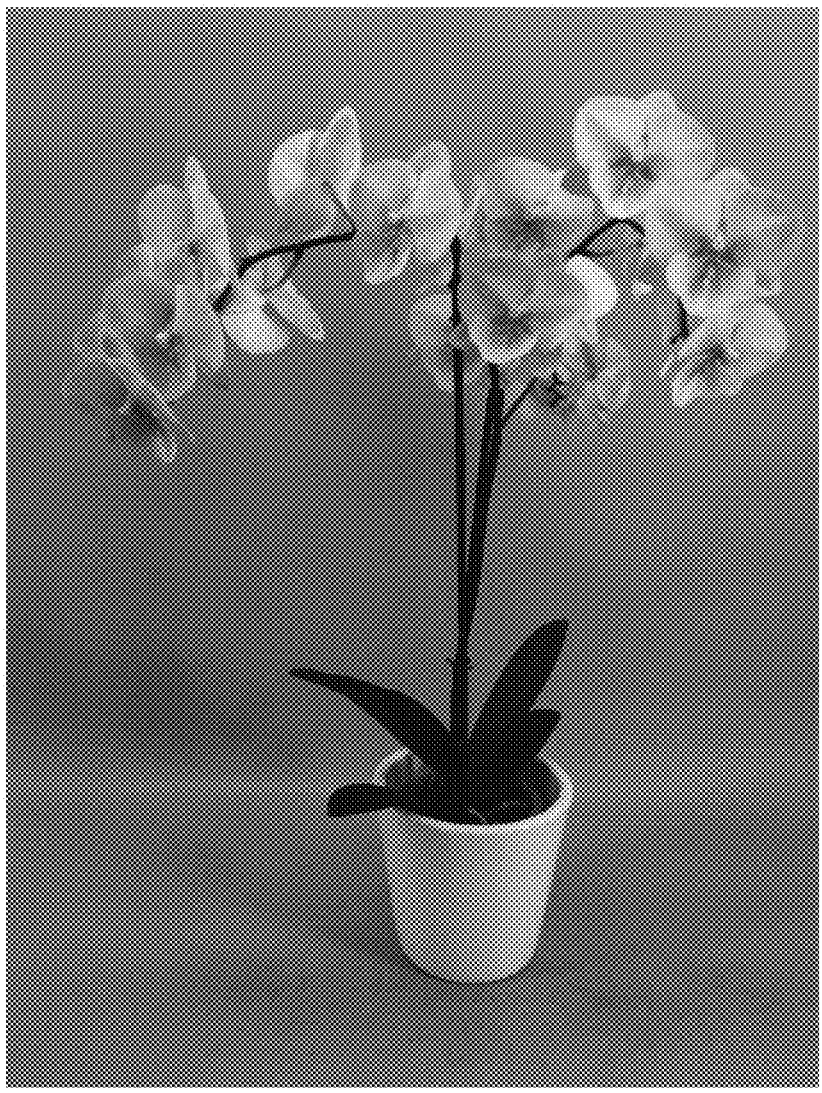
FIG. 1 shows the overall plant habit, including blooms and foliage of 'PHALISYCH'.
Figure 2:
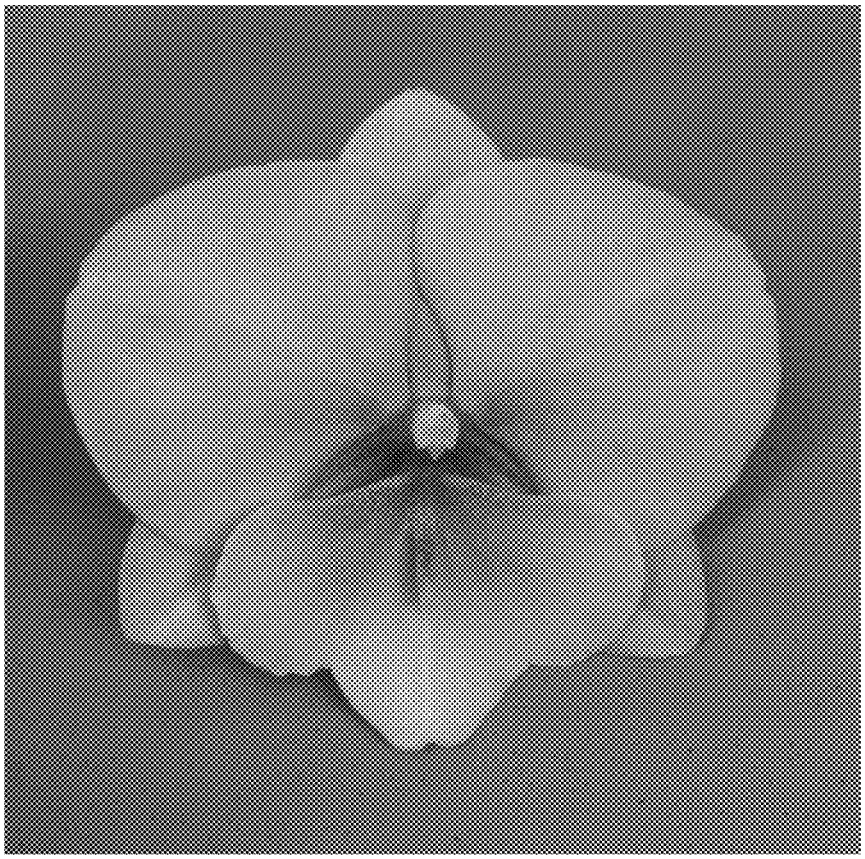
FIG. 2 shows a close-up of a flower of 'PHALISYCH'.
Figure 3:
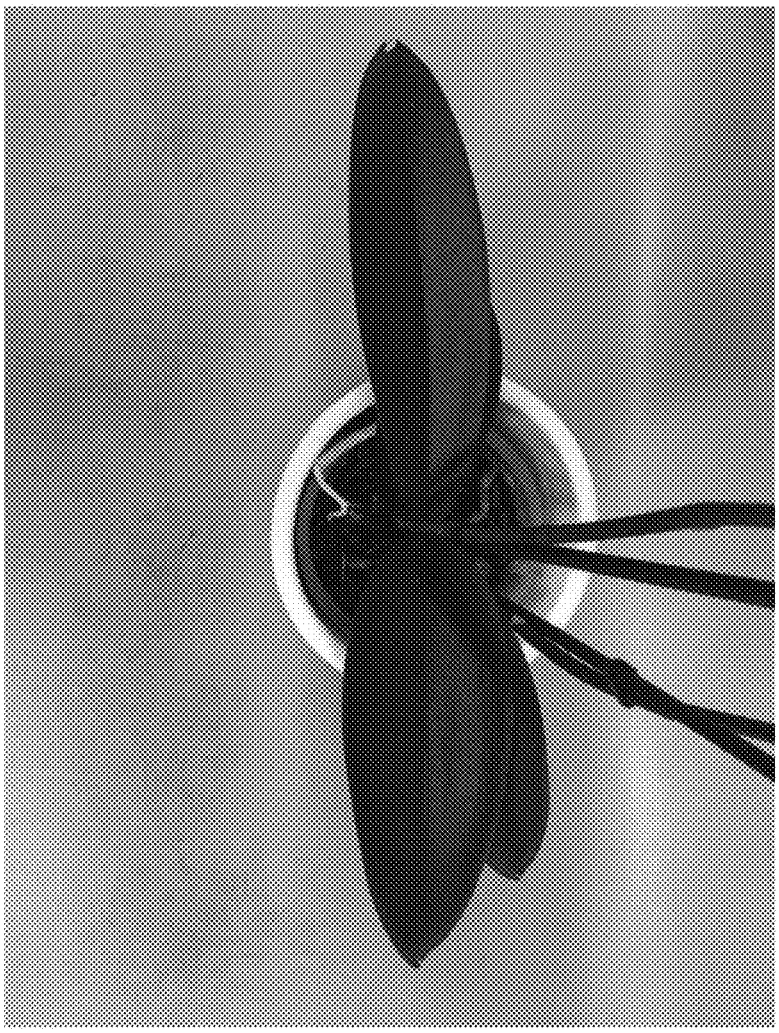
FIG. 3 shows an overhead view of the leaves of 'PHALISYCH'.

The following detailed description sets forth the distinctive characteristics of 'PHALISYCH'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALISYCH'.

Parentage:

*Female parent*.—*Phalaenopsis* cultivar 'E0000298' (unpatented).

*Male parent*.—*Phalaenopsis* cultivar 'E0000299' (unpatented).

Propagation:

*Type*.—Meristem tissue culture.

Roots:

*Root description*.—Greyed-green (something in between RHS 190B and 190C) colored roots with branching lateral roots having light yellow-green (RHS 144D) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height* (*from soil level to top of inflorescence*).—Approximately 53.0 cm to 58.0 cm.

*Width* (*measured from leaf tips*).—About 30.0 cm to 33.0 cm.

*Vigor*.—Strong.

Leaves:

*Mature leaves*.—Quantity per plant: 6 to 7 leaves are produced before flowering. Length (fully expanded): 16.0 cm to 19.0 cm. Width: 5.5 cm to 6.5 cm. Position of the broadest part of the leaf: At the middle. Shape: Narrow oblong. Base shape: Moderately elongated. Apex: Obtuse asymmetric. Leaf blade angle with the petiole (measured from the horizontal position): Between 20 degrees and 35 degrees. Leaf margin: Entire. Color: Upper surface: RHS 147A with a purple-dark red margin (something in between RHS N77A and RHS 187A) toward the tip. Lower surface: Mix of RHS 147B and something in between RHS N77A and RHS 187A. Texture (both upper and lower surfaces): Smooth. Thickness: 2.1 mm to 2.4 mm. Variegation: Absent. Venation: Pattern: Parallel. Color of the midvein: Upper surface: RHS 147A with a hint of something in between RHS N77A and RHS 187A. Lower surface: RHS N77A.

Peduncle:

*Quantity per plant*.—1 to 3.

*Number of flowers per peduncle*.—10 to 12.

*Length*.—53.0 cm to 58.0 cm.

*Diameter*.—4.9 mm to 5.3 mm.

*Strength*.—Strong.

*Aspect*.—Upright to slightly pendent.

*Texture*.—Smooth.

*Color*.—Reddish-brown (RHS 200A).

*Internode length*.—4.0 cm to 5.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 3.

*Inflorescence size*.—Height (from base to tip): 240.0 mm to 270.0 mm.

*Flowering time*.—First flowers can be expected 10 to 11 months after planting in a 12-cm pot.

*Flower*.—Height: 80.0 mm to 85.0 mm. Diameter: 82.0 mm to 87.0 mm. Depth of lip: About 2.0 mm.

*Flower longevity*.—On the plant: 9 to 11 weeks.

*Flower shape*.—Flat.

*Fragrance*.—Absent.

*Flower bud*.—Average size: Large. Length: 25.0 mm to 27.0 mm. Width: 20.0 mm to 22.0 mm. Shape: Egg shaped. Color: Yellow-green (RHS 154C) with a touch of red (RHS 184B).

*Petals*.—Arrangement: Touching to slightly overlapping. Shape: Semi-circular. Apex: Emarginated asymmetric. Margin: Entire. Length (from base to tip): 38.0 mm to 40.0 mm. Width: 49.0 mm to 51.0 mm. Position of the broadest part of the petal: Toward the base. Color (when fully opened): Upper surface: Basic color: Yellow (something in between RHS 8A and RHS 8B). Over color: Hint of dark purplish-pink (RHS 186C) at the base. Lower surface: Basic color: Light greenish-yellow (something in between RHS 8B and RHS 8C). Over color: White (RHS NN155C) and purplish-pink (RHS 186D) at the base. Number of spots and stripes on the petals (upper surface): None. Color of spots and stripes on the petals (upper surface): None. Density of netting of the petals (upper surface): None. Color of the netting (upper surface): None.

*Dorsal sepal*.—Shape: Elliptic. Apex: Emarginated symmetric. Margin: Entire. Length (from base to tip): 44.0 mm to 46.0 mm. Width: 29.0 mm to 31.0 mm. Position of the broadest part of the dorsal sepals: At the middle. Color (when fully opened): Upper surface: Basic color: Yellow (something in between RHS 8A and RHS 8B). Over color: Dark purplish-pink (RHS 186C) at the base. Lower surface: Basic color: Light greenish-yellow (something in between RHS 8B and RHS 8C). Over color: Purplish-pink (RHS 186D) at the base and diluting red region (RHS 181C) toward the margin and tip.

Number of spots and stripes on the dorsal sepals (upper surface): None. Color of spots and stripes on the dorsal sepals (upper surface): None. Density of netting of the dorsal sepals (upper surface): None. Color of the netting (upper surface): None.

*Lateral sepals*.—Shape: Ovate. Apex: Obtuse asymmetric. Margin: Entire. Length (from base to tip): 43.0 mm to 45.0 mm. Width: 27.0 mm to 29.0 mm. Position of the broadest part of the lateral sepals: Toward the base. Color (when fully opened): Upper surface: Basic color: Yellow (something in between RHS 8A and RHS 8B). Over color: Dark purplish-pink (RHS 186C) at the base. Lower surface: Basic color: Light greenish-yellow (something in between RHS 8B and RHS 8C). Over color: Light greenish-yellow (RHS 4C) and purplish-pink (something in between RHS 186C and RHS 186D) at the base; purplish-red middle vein (RHS 184C) and diluting purplish-red region (RHS 184D) toward the tip. Number of spots, dots, and stripes on the lateral sepals (upper surface): Medium number of very small dots at the base. Color of spots, dots, and stripes on the lateral sepals (upper surface): RHS 186A. Density of netting of the lateral sepals (upper surface): None. Color of the netting (upper surface): None.

*Labellum* (*lip*).—Overall shape: Three-lobed with callus at central junction of the lateral lobes and base of the apical lobe. Lateral lobes and apical lobe are connected. Whiskers: Absent. Length of whiskers: Not applicable. Color of whiskers: Not applicable.

*Lateral lobe*.—Margin: Crenulated. Length: 24.0 mm to 26.0 mm. Width: 19.0 mm to 21.0 mm. Color: Upper surface: Slightly light reddish-purple (RHS N75C) and white (RHS NN155C) at the base; yellowish-pink (RHS 181D) toward the middle; light yellow-green (RHS 8B) toward the tip. Lower surface: White (RHS N155C) at the base; purplish-pink (RHS 186D) on one side and light greenish-yellow (RHS 4C) toward the other side. Number of spots, dots, and stripes on the lateral lobe: Medium number of very small dots at the base. Color of spots, dots, and stripes on the lateral lobe: RHS 181C. Density of netting of the lateral lobe: None. Color of the netting: None.

*Apical lobe*.—Shape: Trapezoid. Margin: Entire. Length: 10.0 mm to 12.0 mm. Width: 23.0 mm to 25.0 mm. Color: Upper surface: Light greenish-yellow (RHS 4C). Lower surface: Light greenish-yellow (something in between RHS 4C and RHS 4D). Number of spots and stripes on the apical lobe: None. Color of spots and stripes on the apical lobe: None. Density of netting of the apical lobe: None. Color of the netting: None.

*Callus*.—Average size: Small. Height: Not applicable. Length: 7.0 mm to 9.0 mm. Diameter: 1.9 mm to 2.2 mm. Color: Light greenish-yellow (RHS 8C); dotted (RHS 181C). Pubescence: Present.

Reproductive organs:

*Column*.—Length: 7.0 mm to 9.0 mm. Diameter: 4.0 mm to 5.0 mm. Color: White (RHS NN155C).

*Pollinia*.—Quantity: 2. Diameter: 0.8 mm to 1.1 mm. Color: Orange-yellow (RHS 23A).

*Ovary*.—Length: 11.0 mm to 13.0 mm. Diameter: 2.2 mm to 2.4 mm.

*Pedicel*.—Length: 36.0 mm to 38.0 mm. Diameter: 2.6 mm to 2.9 mm. Texture: Smooth. Color: Hint of dark red (RHS 187A) at the base; light yellow-green (RHS 145C) and mix of light purple (RHS 76A) and reddish-purple (RHS N78B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALISYCH', cultivar 'E0000298' (unpatented), is no longer in existence, therefore a meaningful comparison cannot be made.

The male parent plant of 'PHALISYCH', cultivar 'E0000299' (unpatented), is no longer in existence, therefore a meaningful comparison cannot be made.

'PHALISYCH' is most similar to the commercial *Phalaenopsis* plants named 'PHALEKDEK' (U.S. Plant Pat. No. 32,024) and 'PHALFOBOK' (unpatented). 'PHALISYCH' differs from the commercial variety 'PHALEKDEK' in that 'PHALISYCH' has trapezoid apical lobes, petals that are touching to slightly overlapping, and no whiskers, whereas 'PHALEKDEK' has triangular apical lobes, petals that are open/free, and whiskers. Additionally, 'PHALISYCH' has smaller flowers than 'PHALEKDEK'.

'PHALISYCH' differs from the commercial variety 'PHALFOBOK' in that 'PHALISYCH' has trapezoid apical lobes, petals that are touching to slightly overlapping, and an extra-large lip type, whereas 'PHALFOBOK' has ovate apical lobes, petals that are open/free, and a normal lip type. Additionally, 'PHALISYCH' has larger flowers than 'PHALFOBOK'.

I claim:

1. A new and distinct variety of *Phalaenopsis* plant named 'PHALISYCH', substantially as described and illustrated herein.

* * * * *